United States Patent [19]

Petersen et al.

[11] 4,295,846

[45] Oct. 20, 1981

[54] PROCESS FOR THE PRODUCTION OF FORMALDEHYDE-FREE FINISHING AGENTS FOR CELLULOSIC TEXTILES AND THE USE OF SUCH AGENTS

[75] Inventors: Harro Petersen, Frankenthal, Fed. Rep. of Germany; Panemangalore S. Pai, Charlotte, N.C.; Friedrich Klippel, Ludwigshafen; Friedrich Reinert, Wachenheim, both of Fed. Rep. of Germany

[73] Assignee: BASF Aktiengesellschaft, Fed. Rep. of Germany

[21] Appl. No.: 131,409

[22] Filed: Mar. 18, 1980

[51] Int. Cl.³ .......................................... D06M 13/34
[52] U.S. Cl. .................................. 8/186; 260/29.4 R; 427/389.9; 528/245
[58] Field of Search .................. 528/245; 260/29.4 R; 8/186; 427/389.9

[56] References Cited

U.S. PATENT DOCUMENTS

| | | | |
|---|---|---|---|
| 3,079,279 | 2/1963 | Van Loo | 260/29.4 |
| 3,488,701 | 1/1970 | Herbes et al. | 8/186 |
| 3,652,583 | 3/1972 | Tajima et al. | 260/29.4 R |
| 3,671,307 | 6/1972 | Spangler | 260/29.4 R |

OTHER PUBLICATIONS

Vail, *Chem. & Ind.*, 1967, pp. 305–309.
Gonzales et al., *Textile Research Journ.*, 1966, pp. 565–571.

*Primary Examiner*—Lorenzo B. Hayes
*Attorney, Agent, or Firm*—Keil & Witherspoon

[57] ABSTRACT

Process for the production of formaldehyde-free finishing agents for textiles containing or consisting of cellulose which is based on the reaction of urea or symmetrically disubstituted urea with glyoxal in the presence of buffer salts and alcohols at a pH of below 7, buffered mixtures of 4,5-hydroxyethyleneureas or N,N'-disubstituted 4,5-dihydroxyethyleneureas partially etherified in 4- and 5-positions being formed.

2 Claims, No Drawings

PROCESS FOR THE PRODUCTION OF FORMALDEHYDE-FREE FINISHING AGENTS FOR CELLULOSIC TEXTILES AND THE USE OF SUCH AGENTS

For the purposes of the invention, finishing means wrinkle-resist and shrink-resist finishing, also referred to as easy-care finishing. This finishing is usually carried out with aminoplast intermediates, i.e., products containing hydroxymethyl or alkoxymethyl groups on the nitrogen, in particular hydroxymethylated or alkoxymethylated ureas, cyclic ureas, carbamates and aminotriazines. On curing or fixing, the N-hydroxymethyl or N-alkoxymethyl groups react, under the influence of heat and catalysts, with each other and with the hydroxy groups of the cellulose, with acetal formation and crosslinking. Normally, a substantial drop in the mechanical strength of the cellulose resulting from this treatment is hardly avoidable. This is a serious disadvantage of textile finishing. A further, very serious disadvantage of finishing with these products is the elimination of formaldehyde during application and the subsequent elimination of formaldehyde on woven fabrics finished with the products.

There have been many attempts to solve the problems of formaldehyde-free finishing. It must be borne in mind that practically all the compounds that are suitable from a chemical point of view, i.e., the aziridine, epoxy, chlorohydroxy, vinyl and acryl compounds, are very toxic and cannot therefore be considered for textile finishing. Furthermore, the desired finishing properties can only be partially achieved with these compounds.

Recently, in connection with formaldehyde-free finishing, the N,N'-dimethyl derivatives of the 4,5-dihydroxyethyleneurea

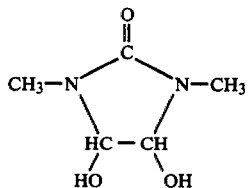

have been discussed and such products have been brought on the market by some Japanese chemical manufacturers.

Earlier work (S. L. Vail, Chem. and Ind. 1967, 305–309 and E. J. Gonzales, R. R. Benerito and R. J. Berni, Textile Research Journal 36 (1966), 365–371) showed that the effects achieved with N,N'-dimethyl-4,5-dihydroxyethyleneurea are more like those of the untreated material than the conventional standard of a resin finished material.

The requirement for formaldehyde-free finishing means that N-hydroxymethyl compounds cannot be used. On toxicological grounds the abovementioned aziridine, epoxy, chlorohydroxy, vinyl or acryl compounds cannot be employed either.

The object of the invention, therefore, is to provide a simple and toxicologically harmless process for the production and use of a formaldehyde-free finishing agent that combines adequate reactivity with a long shelf life, adequate yield and high stability of the finishing liquors prepared therefrom and is also sufficiently hydrolysis-resistant to make the finished textile substantially and permanently shrink and wrinkle resistant. Furthermore the decreases in tear and abrasion resistance should not be greater, if possible even less, than when conventional finishing agents are used, and the hand should not if possible be adversely affected by the finishing.

We have found a process for the production of liquid easy-care finishing agents for cellulosic textiles that satisfies all these requirements. The process is based on the reaction of urea or preferably symmetrically disubstituted ureas I in aqueous solution with glyoxal in the presence of buffer salts and alcohols at a pH in the range of 4 to 6.8, preferably 5 to 6.5, to form 4,5-dihydroxyethyleneureas, or preferably N,N'-disubstituted 4,5-dihydroxyethyleneureas II, partially etherified in 4- or 5-position:

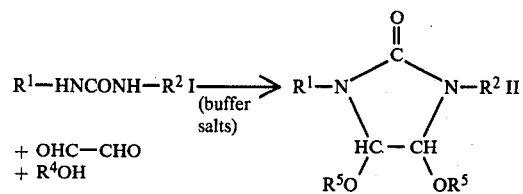

$R^1$ and $R^2$ are hydrogen, preferably $-[(CH_2)_nO]_{\overline{m}}R^3$, $R^3$ is $C_{1-4}$ alkyl, preferably methyl, or, if $m>0$, hydrogen, $R^4$ is $-[(CH_2)_nO]_{\overline{m}}R^3$, preferably methyl, $R^5$ is hydrogen and $R^4$, 0 to 75, preferably 10 to 60% being H and the remainder $R^4$, n is 2–4, preferably 2 and 3, especially 2, and m is 0–10, preferably 0–5.

The reaction is carried out in two stages, initially without the alcohol $R^4OH$ for at least 3, preferably 4 to 5 hours, at a pH of 4 to 6.8, preferably 5 to 6.5, and at a temperature of 20 to 60, preferably 30° to 40° C., and then, after the alcohol has been added, for 1 to 4, preferably 2 to 3 hours, at a pH of 2 to 4.5, preferably 2.5 to 4, and at a temperature of 30 to 65, preferably 40° to 55° C. Finally a pH of 4 to 7, preferably 4.5 to 6.5, is set up. During the first 2 hours of the 1st stage 45° C. should not be exceeded.

Examples of symmetrically disubstituted ureas that can be used are N,N'-dimethylurea, N,N'-diethylurea, N,N'-diisopropylurea, N,N'-di-n-butylurea, N-methyl-N'-ethylurea, N,N'-di-hydroxyethylurea, N,N'-dimethoxyethylurea and N,N'-dimethoxypropylurea.

Suitable alcohols $R^4OH$ are, for example, methanol, ethanol, methylglycol, ethyleneglycol, methyldiglycol and polyetherdiols. Since the hydroxyl groups in 4- and 5-position on the cyclic urea II are to be at least 25% etherified, at least 0.5 mole, preferably 1 to 2 moles, of alcohol $R^4OH$ is to be used per mole of urea. There is no fixed upper limit for the amount of alcohol but there is little point in using substantially more than 2 moles per mole of urea, because the solution is diluted unnecessarily.

Examples of buffer mixtures that can be used are alkali metal acetates/acetic acid, alkali metal tartrates/tartaric acid, alkali metal citrates/citric acid, alkali metal phthalates/phthalic acid, alkali metal glycolates/glycolic acid and mixtures thereof. It is known that buffer mixtures are generally mixtures of salts of weak acids with any acids and this is also the case here. The amounts in which they are used should be so chosen that, under the expected conditions, it is certain that the desired pH range (here 4 to 6.8, preferably 5 to 6.5) will be maintained. For the process of the invention as little as 2% by weight, with reference to the urea used as starting compound, of a salt of a weak acid, e.g. sodium acetate, may be sufficient. As a rule 5% to 15% by weight is used. There is no upper limit to the quantity, but there is little point in using more than 20% by weight.

In the conventional production of N,N'-dimethyl-4,5-dihydroxyethyleneurea solid symmetrical dimethylurea is reacted with the aqueous solution of glyoxal (e.g. 40%) in a molar ratio of 1:1 in the weakly acid or weakly alkaline range at a temperature of between 20° and 60° C. Cyclization to N,N'-dimethyl-4,5-dihydroxyethyleneurea proceeds relatively slowly and needs reaction times of up to 2 days for a conversion of more than 90%. The reaction requires several weeks to bind all the glyoxal under these reaction conditions. An increase in the temperature causes considerable discoloration of the product. Residual amounts of unreacted glyoxal give rise to heavy yellowing to browning when the fabric is finished. It is possible to separate the N,N'-dimethyl-4,5-dihydroxyethyleneurea contained in the reaction mixture by filtering it after it has been cooled and crystallized, and, if desired, purify it by recrystallization. However, these measures involve considerable losses in yield. Apart from this, neither the crude nor the purified solutions of N,N'-dimethyl-4,5-dihydroxyethyleneurea are very suitable as finishing agents for cellulosic textiles, as can be seen from Comparative Experiment 2. Comparative Experiment 3 shows that even the etherification or, more precisely, the acetalization of the OH groups in positions 4 and 5 with alcohols only partially reduces the yellowing of the fabric during finishing. Further investigations have shown, that, under the action of acids, for example latent acid catalysts, during resin finishing, the 4,5-dihydroxyethyleneureas are converted to hydantoins and other strongly colored byproducts (H. Peterson, Textilveredlung 3 (1968), 51–62). Under the action of acids or latent acid catalysts, the 4,5-dihydroxyethyleneureas can also be converted under heat to glyoxaldiureins with the liberation of glyoxal. Liberated glyoxal also causes, as has already been mentioned, yellowing of the fabric.

Surprisingly, when the process of the invention is used for the production of 4,5-dihydroxyethyleneureas or N,N'-disubstituted 4,5-dihydroxyethyleneureas partially acetalized with alcohols, practically all the desired properties can be achieved and the undesirable side reactions avoided. In the presence of buffer mixtures, the reaction of urea or symmetrically disubstituted ureas with glyoxal to 4,5-dihydroxyethyleneureas or N,N'-disubstituted 4,5-dihydroxyethyleneureas is accelerated to such an extent that cyclization is quantitatively complete after only a few hours at temperatures of below 50° C. without the reaction solution becoming discolored. No further free glyoxal is detectable in the reaction mixture. In the presence of buffer substances the reaction proceeds without the formation of byproducts and leads to a one hundred percent yield. Purification is therefore no longer necessary. To achieve optimum properties the reaction mixtures obtained are partially acetalized with alcohols in the presence of acids and can be used direct for textile resin finishing. In addition to these surprising findings (short reaction times, quantitative yield, no byproducts formed and no residual glyoxal), a further very interesting effect was discovered when finishing cellulosic fabrics with the buffered reaction mixtures; if unbuffered solutions of e.g., N,N'-dimethyl-4,5-dihydroxyethyleneurea III or N,N'-dimethyl-4,5-dimethoxyethyleneurea IV are employed in the resin finishing of cellulosic textiles under the conventional conditions of application, no acceptable finishing effects are achieved and heavy yellowing of the fabric is observed when III is used, as Comparative Experiments 2 and 3 show.

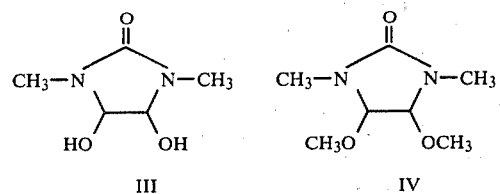

When the products obtained in accordance with the invention, i.e. the solutions of compounds II prepared using buffer mixtures are employed, finishing effects are achieved on the cellulose-containing fabric with low shrink values, high Monsanto ratings and durable press values with low decreases in tear and abrasion resistance and without discoloration. The hand of the fabric remains soft. The wettability and moisture take-up are scarcely affected as compared with the non-finished fabric.

The production process of the invention is advantageously carried out by reacting a 40% aqueous glyoxal solution with powdered urea of N,N'-disubstituted urea, the solution being adjusted to pH 1–2 with sulfuric acid, hydrochloric acid or another acid and such an amount of an alkali metal salt of an organic acid, e.g., sodium acetate or sodium citrate, being added before, immediately after or simultaneously with the addition of urea that a pH of 4–6.8, preferably 5–6.5, is set up. The reaction temperature is kept below 50° C. at least during the first two hours. After stirring for about 4–5 hours at between 30° and 40° C. the reaction is finished. As mentioned before, it has proved advantageous to acetalize the OH groups in 4- and 5-positions partially with alcohols. For this purpose, for example methanol or another alcohol, specified above as R⁴OH, is added to this solution, the pH is adjusted to 2.5–4 with a mineral acid and the whole stirred for 2–3 hours at 40°–55° C. The mixture can then be adjusted to pH 4.5–6.5 with alkaline solution or an alkali metal salt of an organic acid, or a buffer salt can be added.

Finishing agents obtained in accordance with the invention have a long shelf life and do not discolor. The aqueous solutions of a pure N,N'-dimethyl-4,5-dihydroxyethyleneurea, on the other hand, become very severely discolored after only a few weeks' storage.

The finishing agents obtained in accordance with the invention may be applied in a conventional manner, namely in the form of an aqueous impregnating bath to which the catalysts which are generally necessary for the crosslinking are added, although the latter may of course in principle be applied in a separate operation (e.g., by padding, spraying or slop padding). Particularly suitable catalysts are potentially acid salts that are generally known and used for purposes of textile finishing. Examples are ammonium salts of strong acids, magnesium chloride, zinc chloride, aluminum chloride, zinc nitrate and salts of fluoroborates. Mixtures of several catalysts may also be used. In many cases it is advantageous to use mixtures of these catalysts with organic acids (e.g., glycolic acid) containing hydroxyl groups.

The amount of catalyst used is generally in the range of 25 to 45, preferably 30 to 40, percent by weight, with reference to the solids content of the finishing agent (crosslinking agent). The concentration of finishing agent in the finishing liquor (calculated as solid) is generally governed by the desired effect. As a rule it is between 25 and 100 g/l. The material to be treated is impregnated with the impregnating liquor in a conventional manner. It is preferable to use a pad; the impregnated material is freed from excess impregnating liquor in a conventional manner, for example by squeezing. The add-on is 2 to 8%, preferably 3 to 6%. The finishing agent can also be applied by a minimum application technique (Triatex process) or via a minimum application technique by a foam application technique. The impregnated fiber fabric can be dried more or less and can then be heated in the presence of acid or potentially acid catalysts at a temperature of between 100° and 230° C., preferably 130° to 210° C. Under these conditions the reaction is generally complete after 20 seconds to 15 minutes. A higher temperature naturally means a shorter time and vice versa. During or after drying, the fabric can be shaped mechanically, for example by stuffing, crimping, ironing, calendering, embossing or pleating. Cellulosic textiles finished in this way are permanently wrinkle and shrink resistant. Further advantages are the soft hand of the finished textiles, low decreases in tear strength, low decreases in abrasion strength, absolute fastness to chlorine and absolute freedom from formaldehyde.

In addition to the finishing agents obtained in accordance with the invention, the conventional water repellent, softening, leveling and wetting agents, resin finishes and agents for modifying the hand can be used. Examples of water repellent agents are aluminum- or zirconium-containing paraffin wax emulsions and silicone-containing formulations. Examples of softening agents are oxyethylation products of higher fatty acids, fatty alcohols and fatty acid amides, relatively high molecular weight polyglycol ethers, higher fatty acids, fatty alcohol-sulfonates and N-stearyl-urea compounds. Examples of leveling agents are water-soluble salts of acidic esters from polybasic acids and ethylene oxide or propylene oxide adducts of relatively long-chain base molecules capable of undergoing oxyalkylation. Examples of wetting agents are salts of alkylnaphthalenesulfonic acids, alkali metal salts of dioctyl sulfosuccinate, and the adducts of alkylene oxides with fatty alcohols, alkylphenols, fatty amines and the like. Examples of resin finishes are cellulose ethers, cellulose esters and alginates, as well as solutions or dispersions of synthetic polymers and polycondensates, e.g., of polyethylene, nylons, oxyethylated nylons, polyvinyl ethers, polyvinyl alcohols, polyacrylic acid, polyacrylates and polyacrylamides, the corresponding polymethacrylic compounds, polyvinyl propionate, polyvinylpyrrolidone, and copolymers, for example of vinyl chloride and acrylic acid esters, of butadiene and styrene or acrylonitrile, or of 1,1-dichloroethylene, β-chloroalkyl acrylates or vinyl ethyl ether and acrylamide, or the amides of crotonic acid and maleic acid. Examples of suitable agents for modifying the hand are polyvinyl acetate and polyacrylates and, if desired, mixtures thereof. Naturally no finishing agents or assistants containing hydroxymethyl or alkoxymethyl groups can be used as finishes absolutely free from formaldehyde. These additional assistants are in general used in amounts of from 0.3 to 4%, preferably 1 to 2.5%, based on the weight of the dry textile, though in special cases these amounts may also be exceeded.

In specific cases, e.g., for the resin finishing of pure cotton fabrics where very high Monsanto ratings are required, the products obtained in accordance with the invention can be used with particular success together with commercial crosslinking silicone elastomers.

The compounds of formula V described in German Pat. No. 2,334,655

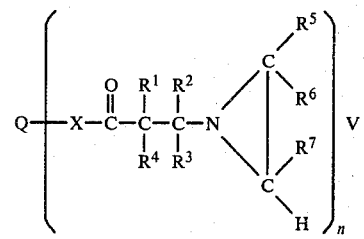

where
R$^1$ to R$^7$ are hydrogen or C$_{1-3}$ alkyl,
Q is the radical of an n-valent alcohol or phenol,
n is 2 or 3, and
X is a polyether chain of butoxy and/or propoxy and, optionally, ethoxy units with a C:O atomic ratio of at least 2.67:1 and a molecular weight of from 150 to 15000 when n=2 and of from 150 to 3000 when n=3, can be used with considerable success instead of or in combination with the silicone elastomers mentioned above.

Suitable cellulosic textiles are mixtures of cotton or regenerated cellulose with man-made fibers, especially with polyester fibers.

The parts and percentages specified in the following Examples are by weight.

EXAMPLE 1

208 parts of a 40% glyoxal solution are placed in a stirred kettle and 1.42 parts of citric acid monohydrates and 4.6 parts of anhydrous sodium acetate are added, the pH of the solution being from 4.6 to 4.7 Then 135 parts of N,N'-dimethylurea are added with cooling, whereby the pH is adjusted to 5.6 to 5.7. After stirring for 4 hours at 30°–35° C., 69 parts of methanol and 14.4 parts of citric acid monohydrate are added and stirring is continued for 2 hours at 50° C. at a pH of approx. 4.2 to 4.3. Then 10.4 parts of anhydrous sodium acetate are added and the pH is adjusted to 5.6 to 5.7 with dilute sodium hydroxide solution. Dilution with 81 parts of water gives a 50% crosslinker solution which is ready for use.

EXAMPLE 2

224 parts of a 40% aqueous glyoxal solution are adjusted to pH 1.2 with about 0.7 part of 75% sulfuric acid in a stirred vessel. Then 146 parts of N,N-dimethylurea and 5 parts of anhydrous sodium acetate are added over 10 minutes with stirring, the pH changing to approx. 6. Stirring is continued for another 4 hours at 40° C. with cooling. Then 74.5 parts of methanol and 2 parts of 75% sulfuric acid are added to the cyclization product, a pH of approx. 3.9 being obtained. After stirring for 2 hours at 50° C., 11.3 parts of anhydrous sodium acetate and 88.5 parts of water are added and the pH is adjusted to approx. 4 with approx. 5 parts of 75% sulfuric acid. 500 parts of a 50% crosslinker solution is obtained which is ready for use.

EXAMPLE 3

A mixture of 656 parts of 40% aqueous glyoxal solution, 428 parts of N,N-dimethylurea and 14.7 parts of anhydrous sodium acetate is adjusted to pH 6.05 with concentrated hydrochloric acid and stirred for 4 hours at 20° to 30° C., intensive cooling being required during the first 2 hours. Then 218 parts of methanol and 12 parts of concentrated hydrochloric acid are added. The reaction mixture, which has a pH of approx. 4, is stirred for 2 hours at 50° C. Then 32.9 parts of anhydrous sodium acetate and 259 parts of water are added and the pH is adjusted to approx. 4.2 with some 29 parts of concentrated hydrochloric acid. 1600 parts of a ready-to-use 50% crosslinker solution is obtained.

EXAMPLE 4

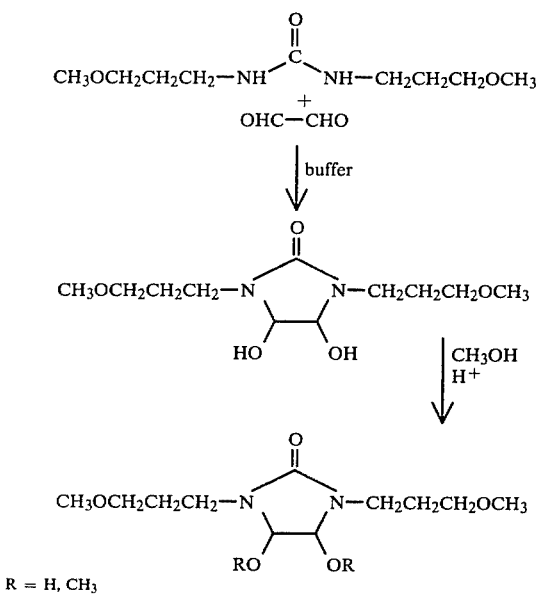

R = H, CH₃

0.2 part of 75% sulfuric acid is added to 145 parts of 40% aqueous glyoxal solution in a stirred vessel. 204 parts of N,N'-bismethoxypropylurea and 3.5 parts of anhydrous sodium acetate are added to the mixture while stirring, a pH of 4.3 being set up. The reaction is kept at 45° C. for 2 hours and at 60° C. for another 2 hours. Then 60 parts of methanol and 3 parts of 75% sulfuric acid are added, the pH changing to approx. 2.8–3.0. After stirring for 2 hours at 50° C., 8 parts of sodium acetate and 310 parts of water are added and the pH is adjusted to 5.0–5.2 with 75% sulfuric acid. 630 parts of a 50% crosslinker solution are obtained.

EXAMPLE 5

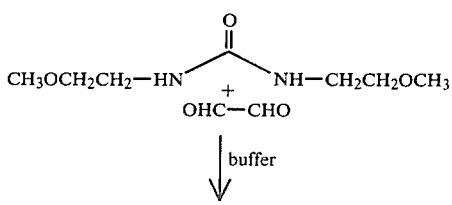

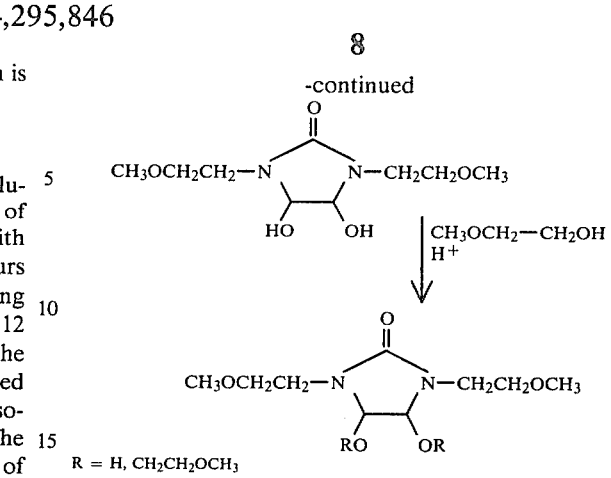

R = H, CH₂CH₂OCH₃

0.4 part of 75% sulfuric acid and 4.5 parts of sodium acetate are added to a mixture of 176 parts of N,N'-bis-methoxyethylurea and 145 parts of a 40% glyoxal solution and the whole is heated in a stirred flask at pH 4 for 2 hours at 45° C. and for another 2 hours at 60° C. with stirring. Then 115 parts of methyl glycol and 3.5 parts of 75% sulfuric acid are added, the pH changing to 2.1. The reaction mixture is heated for 2 hours at 50° C. 340 parts of water are then added and the pH is adjusted to approx. 5.5 with 50% sodium hydroxide solution. 700 parts of about 50% crosslinker solution is obtained. The solution may be discolored with active carbon and filtered.

EXAMPLE 6

15 parts of citric acid monohydrate and 40 parts of sodium acetate are added to 1,450 parts of 40% aqueous glyoxal solution in a stirred vessel. Then 600 parts of urea are added with stirring, a pH of 4.3 to 4.5 being set up. The mixture is stirred for 5 hours at 35°–40° C. and then 600 parts of methanol and 5 parts of 75% sulfuric acid are added, the pH changing to approx. 3.5. Stirring is continued for another 2 hours at 50° C. and a pH of 4 is adjusted with sodium acetate. 2,700 parts of an about 45% ready-to-use crosslinker solution are obtained.

EXAMPLE 7

The material is to be finished is unbleached 100% cotton cloth having the following properties:

| | |
|---|---|
| Wet crease angle (total of warp and weft = W + W) | 120° |
| Dry crease angle (W + W) | 85° |
| Monsanto rating (machine-dry = md) after 20-minute wash at 60° C. | 2 |
| Tensile strength, weft | 470 N |
| Shrinkage after single wash at 60° C., warp | 4.0% |
| weft | 3.0% |

The cloth is padded with an aqueous solution of 150 g/l of 50% crosslinker solution prepared as described in Example 1 and 30 g/l of magnesium chloride hexahydrate as catalyst, squeezed to a wet pickup of approx. 70%, dried at 110° C. to approx. 8% residual moisture and condensed for 4 minutes at 150° C. The cloth thus finished has the following properties:

| | |
|---|---|
| Wet crease angle (W + W) | 210° |
| Dry crease angle (W + W) | 198° |
| Monsanto rating, md, after 20-minute wash at 60° C. | 3.75 |

-continued

| | |
|---|---|
| Tensile strength, weft | 360 N |
| Shrinkage after single wash at 60° C., warp | 1.0% |
| weft | 0.0% |
| Free formaldehyde according to LAW 112-1973 | 0 ppm |

EXAMPLE 8

Cotton cloth as described in Example 7 is padded in a conventional manner with the following liquor:
- 150 g/l of 50% crosslinker solution as described in Example 1
- 10 g/l of a commercial 35% aqueous emulsion of a high molecular weight aminosiloxane
- 5 g/l of a commercial 30% aqueous emulsion of a relatively low molecular weight polysiloxane as crosslinker
- 3 g/l hydrogen peroxide, 35%
- 30 g/l magnesium chloride hexahydrate and squeezed to a wet pickup of approx. 70%. Drying and condensation are carried out as described in Example 7. Application tests give the following results:

| | |
|---|---|
| Wet crease angle (W + W) | 247° |
| Dry crease angle (W + W) | 266° |
| Monsanto rating, md, after 20-minute wash at 60° C. | 4 |
| Tensile strength, weft | 320 N |
| Shrinkage after single wash at 60° C., warp | 0.0% |
| weft | 0.5% |
| Free formaldehyde according to LAW 112-1973 | 0 ppm |

The handle is very good and there is a distinct improvement in sewability.

EXAMPLE 9

Cotton cloth as described in Example 7 is padded with the following liquor:
- 150 g/l 50% crosslinker solution as described in Example 1
- 30 g/l of a solution of 20 g of a mixture of 50 parts of polytetrahydrofuran-2000$^{(x)}$-bis-($\beta$-aziridinopropionic acid ester), 5 parts of an adduct of 7 moles of ethylene oxide and a $C_{12-14}$ alcohol and 45 parts of methanol in 10 g 1 N acetic acid
- 30 g/l magnesium chloride hexahydrate and squeezed to a wet pickup of approx. 70%.

(x) Mean molecular weight of polytetrahydrofuran chain

Drying and condensation are carried out as described in Example 7. Application tests give the following results:

| | |
|---|---|
| Wet crease angle (W + W) | 236° |
| Dry crease angle (W + W) | 251° |
| Monsanto rating, md, after 20-minute wash at 60° C. | 4 |
| Tensile strength, weft | 350 N |
| Shrinkage after single wash at 60° C., warp | 0.5% |
| weft | 0.5% |
| Free formaldehyde according to LAW 112-1973 | 0 ppm |

A silky handle is obtained which is resistant to washing. Sewability is improved.

EXAMPLE 10

Cotton cloth as described in Example 7 is padded with the following liquor:
- 150 g/l 50% crosslinker solution as described in Example 2
- 30 g/l of a commercial softener based on a fatty acid condensation product
- 30 g/l magnesium chloride hexahydrate and squeezed to a wet pickup of approx. 70%. Drying and condensation are carried out as described in Example 7. Application tests give the following results:

| | |
|---|---|
| Wet crease angle (W + W) | 221° |
| Dry crease angle (W + W) | 210° |
| Monsanto rating, md, after 20-minute wash at 60° C. | 4 |
| Tensile strength, weft | 350 N |
| Shrinkage after single wash at 60° C., warp | 0.0% |
| weft | 0.5% |
| Free formaldehyde according to LAW 112-1973 | 0 ppm |

EXAMPLE 11

Cotton cloth as described in Example 7 is padded with the following liquor:
- 150 g/l of 50% crosslinker solution obtained according to Example 3
- 30 g/l of a commercial textile softener based on textile wax
- 20 g/l of a commercial hand modifier based on a mixture of polyacrylate and polyvinyl acetate
- 30 g/l of magnesium chloride hexahydrate and squeezed to a wet pickup of approx. 70%.

Drying and condensation are carried out as described in Example 7. A slightly stiff hand and the following other properties are obtained:

| | |
|---|---|
| Wet crease angle (W + W) | 210° |
| Dry crease angle (W + W) | 198° |
| Monsanto rating, md, after 20-minute wash at 60° C. | 3.75-4 |
| Tensile strength, weft | 360 N |
| Shrinkage after single wash at 60° C., warp | 0.0% |
| weft | 0.5% |
| Free formaldehyde according to LAW 112-1973 | 0 ppm |

EXAMPLE 12

A pad bath composition (a) having a pH of approximately 4.2 is prepared by mixing together 10% of the 50% by weight solution of Example 1, 0.2% of i-octyl phenol reacted with 6 moles of ethylene oxide (EO), 1% of a 25% aqueous emulsion of a non-ionic polyethylene softener, 3% of a 45% aqueous emulsion of polyvinyl acetate, 2% of a 25% aqueous zinc nitrate solution and water to make up 100%.

Different types of fabric are then padded with the foregoing padding solution to obtain about 55% wet pickup. Applications of this padding solution are made to 50/50 polyester/cotton sheeting fabric (108 g/m$^2$), bleached, white, and 65/35 polyester/cotton twill fabric (202 g/m$^2$) dyed to a Royal Blue shade using disperse/vat colors.

Each padded fabric is dried at 107° C. for 1 minute and then cured at 150° C. for 1.5 minutes in the precure applications. Additionally the dried (sensitized) fabrics are creased and post-cured between 120° and 163° C. for 8-15 minutes in ovens to simulate the garment industry processes for permanent press slacks. The resulting treated fabrics are essentially free of any objectionable odor and the whiteness or the dyed shade of fabrics is unimpaired by the treatment.

A control experiment (b) is carried out using 10% of a 50% aqueous solution of dimethylol glyoxal monourein and 2.5% of a 25% aqueous solution of zinc nitrate, the remaining ingredients being the same as in the previous experiment (a).

Samples of polyester/cotton fabrics treated by the precure finishing method are subjected to 5 launderings in an automatic home type washer using a detergent, and the fabrics are then tumble dried. The properties of the fabrics are tabulated below.

| | | After 5 Home Launderings | |
|---|---|---|---|
| Fabric Type | Treat-ment | Durable Press Ratings AATCC Test Method 125-1975 | % Shrinkage (Warp × Weft) AATCC Test Method 135-1973 |
| 50/50 Polyester/ Cotton Sheeting Fabric | (a) | 4.0 | 1.1 × 0.6 |
| | (b) | 4.0 | 0.9 × 0.8 |
| 65/35 Polyester/ Cotton Sheeting Fabric | (a) | 3.9 | 1.9 × 0.9 |
| | (b) | 3.8 | 2.0 × 0.8 |

From the above data, it can be seen that the product of this invention shows similar properties of durable press and dimensional stability to the conventional dimethylol glyoxal monourein crosslinking agent.

In the manufacture of post-cure durable press garments, the sensitized fabric may be packaged and stored for prolonged periods before it is cut to pattern, sewn, trimmed and then shaped by pressing to introduce creases, pleats, etc., and to smooth the garment in its final configuration. For this reason, the sensitized fabric treated with the product of this invention (a) is studied under the delayed time/temperature during conditions.

| Fabric | Sample No. | Creased Under Hot Head Press and Post-Cured at | |
|---|---|---|---|
| | | Temperature (°C.) | Time (min) |
| 65/35 Polyester/ Cotton Twill, Royal Blue Shade | 1 | 120 | 15 |
| | 2 | 127 | 15 |
| | 3 | 135 | 15 |
| | 4 | 150 | 15 |
| | 5 | 150 | 8 |
| | 6 | 163 | 8 |

Appearance of creases in wash-and-wear items after home laundering is tested by AATCC Test Method 88C-1975. This method is designed for evaluating the retention of pressed-in creases in wash-and-wear fabrics. The method is also expected to be applicable to the evaluation of creases in finished garments.

| Sample No. | After 5 Home Launderings | |
|---|---|---|
| | Crease Ratings | % Shrinkage (Warp × Weft) |
| 1 | 4.2 | 2.3 × 1.1 |
| 2 | 4.2 | 2.35 × 1.1 |
| 3 | 4.1 | 2.6 × 1.0 |
| 4 | 4.3 | 2.7 × 1.15 |
| 5 | 4.2 | 2.4 × 1.05 |
| 6 | 4.0 | 2.4 × 1.1 |

The properties of fabric finished by the delayed-cure process are satisfactory over a wide range of crosslinking temperatures. The high reactivity of the product permits treatment of the fiber under very moderate conditions, thus avoiding any degradation of the cellulose.

Other textile data of the post-cured fabrics treated with padding bath compositions (a) and (b) are shown in the following table:

| | Treatment (a) | Treatment (b) |
|---|---|---|
| Acid Perspiration - Shade Change | 4.5 | 4.5 |
| - Stain | 5 | 5 |
| (AATCC Test Method 15-1976) | | |
| Wash Fastness (70° C.) - Shade Change | 4.25 | 4.5 |
| - Stain | 3.0 | 3.5 |
| (AATCC Test Method 61-1975) | | |
| Crocking - Dry | 4.5 | 4.5 |
| - Wet | 3.75 | 3.5 |
| (AATCC Test Method 116-1977) | | |
| Light Fastness - Carbon Arc 40 hrs. | 3.5 | 3.75 |
| (AATCC Test Method 16A-1977) | | |
| Gas Fastness (AATCC Test Method 23-1975) | 4 | 4 |
| Ozone Fastness (AATCC Test Method 159-1975) | 4 | 4 |
| Pilling Resistance (ASTM-D1375-1973) | 4 | 4 |
| Needle Burn | ok | ok |
| Tensile Strength - Warp | 946 N | 950 N |
| - Weft | 559 N | 426 N |
| (ASTM Test Method D1682-84 1975) | | |
| Tongue Tear - Warp | 5800 g | 5800 g |
| - Weft | 4400 g | 4300 g |
| (ASTM Test Method D2261-71) | | |
| Fabric Formaldehyde Content | 0 ppm | 710 ppm |
| (AATCC Test Method 112-1975) | | |

Ratings:
5 = Best
1 = Poor

It can be readily noted that the textile data of treatment (a) are as good as those of treatment (b), the only exception being that treatment (a) shows the absence of formaldehyde, whereas treatment (b) produces fabrics having free formaldehyde thereon.

EXAMPLE 13

Cotton cloth as described in Example 7 is padded with the following liquor:
200 g/l of 50% crosslinker solution prepared according to Example 4
30 g/l magnesium chloride hexahydrate,
squeezed to a wet pickup of approx. 70%, dried at 110° C. to approx. 8% residual moisture and condensed for 4 minutes at 150° C. Application tests give the following results:

| | |
|---|---|
| Wet crease angle (W + W) | 195° |
| Dry crease angle (W + W) | 204° |
| Monsanto rating, md, after 20-minute wash at 60° C. | 3.75 |
| Tensile strength, weft | 25.2 Kp |
| Shrinkage after single wash at 60° C., warp | 1.0% |
| weft | 1.0% |
| Free formaldehyde according to LAW 112-1973 | 0 ppm |

EXAMPLE 14

Cotton cloth as described in Example 7 is padded with an aqueous solution of 200 g/l of 45% crosslinker solution prepared according to Example 6 and 45 g/l of magnesium chloride hexahydrate as catalysts, squeezed to a wet pickup of approx. 70%, dried at 110° C. to 7-8% residual moisture and condensed for 5 minutes at 145° C. Application tests give the following results:

| | |
|---|---|
| Wet crease angle (W + W) | 196° |
| Dry crease angle (W + W) | 176° |
| Monsanto rating, md, after 20-minute wash at 60° C. | 3.5 |
| Tensile strength, weft | 350 N |
| Shrinkage after single wash at 60° C., warp | 1.2 |
| weft | 0.8 |

COMPARATIVE EXPERIMENT 1

Cotton cloth as described in Example 7 is padded with the following liquor:

120 g/l of a 50% aqueous solution of N,N'-dimethylol-4,5-dihydroxyethyleneurea 18 g/l magnesium chloride hexahydrate, squeezed to a wet pickup of approx. 70%, and dried and condensed as described in Example 7. Application tests give the following results:

| | |
|---|---|
| Wet crease angle (W + W) | 246° |
| Dry crease angle (W + W) | 275° |
| Monsanto rating, md, after 20-minute wash at 60° C. | 4.75 |
| Tensile strength, weft | 274 N |
| Shrinkage after single wash at 60° C., warp | 0.0% |
| weft | 0.2% |
| Free formaldehyde according to LAW 112-1973 | 650 ppm |

COMPARATIVE EXPERIMENT 2

Cotton cloth as described in Example 7 is padded with the following liquor:

150 g/l N,N'-dimethyl-4,5-dihydroxyethyleneurea 30 g/l magnesium chloride hexahydrate squeezed to a wet pickup of approx. 70%, and dried and condensed as described in Example 7. Application tests give the following results:

| | |
|---|---|
| Wet crease angle (W + W) | 176° |
| Dry crease angle (W + W) | 168° |
| Monsanto rating, md, after 20-minute wash at 60° C. | 3.0 |
| Tensile strength, weft | 396 N |
| Shrinkage after single wash at 60° C., warp | 1.5% |
| weft | 0.8% |
| Free formaldehyde according to LAW 112-1973 | 0 ppm |

The material shows fairly strong yellowing.

COMPARATIVE EXPERIMENT 3

Cotton cloth as described in Example 7 is padded with the following liquor:

150 g/l N,N-dimethyl-4,5-dimethoxyethyleneurea, unbuffered 30 g/l magnesium chloride hexahydrate, squeezed to a wet pickup of approx. 70%, and dried and condensed as described in Example 7. Application tests give the following results:

| | |
|---|---|
| Wet crease angle (W + W) | 123° |
| Dry crease angle (W + W) | 90° |
| Monsanto rating, md, after 20-minute wash at 60° C. | 2 |
| Tensile strength, weft | 400 N |
| Shrinkage after single wash at 60° C., warp | 4.0% |
| weft | 3.0% |
| Free formaldehyde according to LAW 112-1973 | 0 ppm |

The material shows distinct yellowing and an unpleasant odor.

We claim:

1. A process for the production of formaldehyde-free, easy-care finishing agents with a long shelf life for textiles containing or consisting of cellulose on the basis of urea or N,N'-disubstituted ureas and glyoxal, comprising in the first stage of the process, reacting 1 to 1.1 mole of urea or symmetrically disubstituted urea of the general formula I $$R^1\text{—HNCONH—}R^2 \qquad \text{I}$$

where $R^1$ and $R^2$ are $\text{-[(CH}_2)_n\text{O]}_{\overline{m}}R^3$ or hydrogen, $R^3$ is $C_{1-4}$ alkyl or, if $m > 0$, hydrogen, n is 2 to 4 m is 0 to 10, for three hours in aqueous solution with 1 mole of glyoxal, in the presence of buffer mixtures sufficient to maintain the pH of the solution between 4 and 6.8, at a temperature of from 20° to 60° C., and, in the second stage, reacting the solution resulting from the first stage, after admixing, with at least 0.5 mole of an alcohol $R^4OH$, where $R^4$ is $\text{-[(CH}_2)_n\text{O]}_{\overline{m}}R^3$, where $R^3$, except for hydrogen; m and n are defined above, and an acid, for one to three hours at a pH of between 2 and 4.5 and a temperature of from 30° to 65° C., and finally adjusting the pH of the solution to 4 to 7.

2. A process for the formaldehyde-free, easy-care finishing of textiles containing or consisting of cellulose by impregnating same with an aqueous solution containing 2.5 to 10% by weight, calculated as solid, of the formaldehyde-free crosslinkable finishing agent of claim 1 and 0.6 to 4% by weight of an acid or acid salt catalyst and fixing by heating for from 10 seconds to 15 minutes at from 100° to 230° C.

* * * * *